United States Patent [19]

Cruz, Jr.

[11] 4,204,992

[45] May 27, 1980

[54] METHOD FOR PREPARING PYROGEN FREE COLLAGEN

[75] Inventor: Mamerto M. Cruz, Jr., Pennington, N.J.

[73] Assignee: Avicon, Inc., Fort Worth, Tex.

[21] Appl. No.: 2,661

[22] Filed: Jan. 11, 1979

Related U.S. Application Data

[63] Continuation-in-part of Ser. No. 828,350, Aug. 29, 1977, abandoned.

[51] Int. Cl.$^2$ .......................... C07G 7/00; C08H 1/06; C08L 89/04
[52] U.S. Cl. .................................. 260/123.7; 106/161
[58] Field of Search ....................... 260/123.7; 106/161

[56] References Cited

U.S. PATENT DOCUMENTS

| | | | |
|---|---|---|---|
| 3,073,702 | 1/1963 | Keil et al. ..................... | 106/161 X |
| 3,445,178 | 5/1969 | Hahn ............................. | 8/94.16 |
| 3,475,404 | 10/1969 | Johnsen et al. ............... | 260/123.7 |
| 3,634,561 | 1/1972 | Hawkins et al. .............. | 264/40 |
| 3,742,955 | 7/1973 | Battista et al. ............... | 106/161 X |
| 3,810,473 | 5/1974 | Cruz et al. .................... | 106/161 X |
| 4,148,664 | 4/1979 | Cruz, Jr. ....................... | 106/161 |

FOREIGN PATENT DOCUMENTS 2635508 2/1977 Fed. Rep. of Germany .
1422795 1/1976 United Kingdom .

OTHER PUBLICATIONS

Chem. Abstracts, vol. 53, 1959, 16482 e-f, Organon.
Chem. Abstracts, vol. 83, 1975, 158589x, Cherkin.
Immunochemistry, 1975, vol. 12, pp. 625–627, Cherkin.

*Primary Examiner*—Howard E. Schain
*Attorney, Agent, or Firm*—G. F. Mueller

[57] ABSTRACT

Collagen, such as, corium, is freed of pyrogenetic substances by processing green corium with aqueous solutions of alkalie or alkaline earth metal hypochlorites, washing with aqueous ethanol and subsequently washing with pyrogen free water.

12 Claims, No Drawings

METHOD FOR PREPARING PYROGEN FREE COLLAGEN

This application is a continuation-in-part of application Ser. No. 828,350, filed Aug. 29, 1977, now abandoned.

This invention relates to a method of preparing pyrogen-free collagen, such as, for example, corium, adapted for use in the manufacture of collagen derived products intended for medical uses, particularly in surgical procedures.

In the preparation of a wide variety of collagen derived products for medical uses, it is necessary that the product be free of microorganisms such as bacteria, yeasts, molds and the like. As is well known, these microorganisms may be destroyed or rendered innocuous readily by sterilization as by subjecting the collagen source material and/or collagen derived product to radiation, bactericides, moldicides, various gases and heat treatment.

Pyrogens, on the other hand, are not living organisms and are not rendered innocuous by bactericides, moldicides and gases and are thermostable. Pyrogens are generally considered to be thermostable products of the growth of strains of bacteria, yeasts and molds, some being soluble and others being insoluble and filterable. In addition to their fever producing affects, pyrogens have physiologic effects on the circulatory system, the endocrine glands and metabolic processes. The rise in body temperature is only one of the manifestations to the introduction of minute quantities of pyrogenetic substances into the animal body and the specific affects will be dependent upon the individual subject. Hence, it is essential that pyrogenetic substances be removed, the microorganisms may be rendered innocuous by a sterilization treatment of the final product.

Animal hides constitute the principle source of corium, commonly termed green corium, the collagen raw material, for the preparation of various medical grade products. For example, a hemostatic mass of fibers consisting of ionizable, partial salts of collagen containing from about 50 to about 90% of the stoichiometric amount of acid, calculated at HCl, may be prepared from such corium, as described in the U.S. Pat. to O. A. Battista, M. M. Cruz, Jr., and M. R. Hait, No. 3,742,955, dated July 3, 1973.

In accordance with the present invention, the hides and the collagen raw material, such as corium, derived from the hides are contaminated with microorganisms and are processed in aqueous solutions of hypochlorous acid or a salt thereof such as alkalie and alkaline earth metal hypochlorites, for example, sodium hypochlorite, washed with aqueous ethanol and washed with pyrogen free water prior to conversion into the desired product.

The hides following skinning are trimmed to remove tails and pates and washed, as in a drum washer, with copious amounts of water containing sodium hypochlorite so as to remove dirt and other foreign matter. The water may contain from 50 to 250 ppm, preferably 50 to 100 ppm, of sodium hypochlorite. The hypochlorite may be obtained from commercial solutions generally containing 5.25% sodium hypochlorite. After the hides are clean, they may be transferred from the drum washer to a holding tank and maintained in water containing from about 50 to 100 ppm, sodium hypochlorite until a batch of a desired quantity is obtained. The green corium is then obtained by removal of the flesh and grain sides of the hide as by splitting operations. The foregoing processing is performed at an abattoir. Generally, the preparation of the medical product is conducted at a location remote from the abattoir. In such instance, the corium is blast frozen and transported in the frozen state to the desired location for conversion into a desired product.

The hypochlorite treatment at the concentrations utilized in producing the corium controls the proliferation of bacterial growth before freezing. It is necessary that the subsequent processing of the corium into the source material for the preparation of the final product be effected under treatment conditions to produce a pyrogen free source material. Where the corium is received in a frozen state, it is thawed by placing in pyrogen free, distilled water containing between about 50 and 250 ppm, preferably 50 to 100 ppm, sodium hypochlorite, the solution having a pH between 7 and 9, preferably pH 7-8. Obviously, where the corium has not been frozen it is maintained in such solution. The surfaces of the sheets are then scraped mechanically while in contact with a hypochlorite solution so as to loosen and/or remove substances such as dirt, loose protein and other foreign material on or embedded in the surfaces. A convenient method of scraping involves brush washing by drawing the corium sheet between two rotating, stiff bristle brushes (stiff nylon bristles) under a copious stream of pyrogen free, distilled water preferably containing the hypochlorite.

Following scraping or brush washing the sheets may be cut into strips for convenience in subsequent processing. The sheets or strips are rinsed thoroughly with pyrogen free distilled water containing the hypochlorite and placed in such solution until required for use.

In the preparation of the collagen derived products, the sheets are removed from the hypochlorite solution and the corium separated from excess solution as by pressing or centrifugation. The corium is washed as by immersing in a mixture of ethanol and water containing from 30–90% ethanol by volume, preferably containing about 70 volumes of ethanol and 30 volumes of pyrogen free, distilled water and the mass agitated for about 15 to 30 minutes. The excess liquid is separated from the corium and treatment with the aqueous alcohol repeated at least once. Preferably, three such aqueous alcohol treatments or washing steps are utilized. The corium is finally washed with copious amounts of pyrogen free water and is used in the preparation of the desired products. All processing is conducted at temperatures not exceeding about 40° C., preferably between the freezing point of the liquid and about 25° C.

The removal of pyrogenetic substances from green corium received in frozen state from an abattoir is illustrated by the following examples:

EXAMPLE 1

A 100 gm. sample of thawed, green corium strips (35% solids) was placed in 2000 gm pyrogen free, distilled water to which had been added 1.96 gm of a 5.25% aqueous solution of sodium hypochlorite. The solution contained approximately 50 ppm sodium hypochlorite and was at a temperature of about 35° C. The mass was stirred gently for about 15 minutes. The strips were scraped with a knife edge, washed with a like solution and placed in a fresh solution of sodium hypochlorite. The strips were removed subsequently, squeezed to remove excess liquid and used in performing a pyrogen test.

EXAMPLE 2

A 200 gm sample of thawed, green corium strips (35% solids) was placed in 1870 gm pyrogen free, distilled water containing approximately 50 ppm sodium hypochlorite at a temperature of about 35° C. and the mass stirred gently for about 15 minutes. The strips were scraped with a knife edge, washed with a like solution, and placed in a fresh solution of sodium hypochlorite. The strips were removed, excess liquid expressed by squeezing and the strips placed in 2000 ml of a mixture containing 70 volumes of ethanol and 30 volumes of pyrogen free, distilled water. The mass was stirred for about 15 minutes, the strips removed, squeezed to express excess liquid and placed in a fresh ethanol-water mixture. The mass was stirred for about 30 minutes, the strips removed subsequently, squeezed and used in performing a pyrogen test.

The conventional test for pyrogens utilized the rabbit as the test animal and three rabbits are used in the test. After establishing the normal temperature of each rabbit, 10 ml of a fluid to be tested per kg of body weight of the rabbit are injected into one marginal ear vein of the rabbit. The change in the rabbit temperature is determined at 1-hour intervals for three hours. A positive test results if any rabbit develops an individual temperature rise of 0.6° C. or more at the end of any hour or if the total of the three rabbits' temperature elevation exceeds 1.4° C.

In the pyrogen test of the material prepared as described in Example 1, a 10 gm sample of the treated corium was rinsed in 100 ml portions of pyrogen free, distilled water four times. The fourth rinse water was heated to 37° C. prior to injecting 10 ml. of the rinse water per kg of body weight into each of three rabbits. The change in temperature as compared to the normal temperature of each rabbit was noted at 1-hour intervals for each rabbit and is reported in Table 1 which follows:

Table 1

| Rabbit | Temperature Change, °C. | | | | |
|---|---|---|---|---|---|
| | 1st hr. | 2nd hr. | 3rd hr. | Total Change | Max. Change |
| A | +0.5° | +0.6° | +0.5° | +1.6° | +0.6° |
| B | +0.2° | +0.1° | −0.1° | +0.2° | +0.2° |
| C | +0.6° | +0.6° | +0.4° | +1.6° | +0.6° |
| | | | Total for 3 rabbits | +3.4° | |

The test indicates the material to be pyrogenic. Washing of the hypochlorite treated corium with pyrogen free water does not remove the pyrogenetic substances.

In a similar manner a 10 gm. sample of the material as described in Example 2 that had been subjected to the aqueous ethanol washing after contact with the hypochlorite solution was rinsed in 100 ml portions of pyrogen free distilled water four times. The fourth rinse water was heated to 37° C. prior to injecting 10 ml of the rinse water per kg of body weight into each of three rabbits and the change in the temperature of each rabbit noted as described above. The results are set forth in Table 2 which follows:

Table 2

| Rabbit | Temperature Change, °C. | | | | |
|---|---|---|---|---|---|
| | 1st hr. | 2nd hr. | 3rd hr. | Total Change | Max. Change |
| D | +0.1° | +0.2° | 0.0 | +0.3° | +0.2° |
| E | 0.0 | +0.1° | +0.1° | +0.2° | +0.1° |
| F | 0.0 | 0.0 | 0.0 | 0.0 | 0.0 |
| | | | Total for 3 rabbits | +0.5° | |

The test shows the material to be non-pyrogenic. Washing after hypochlorite treated corium with the aqueous alcohol and pyrogen free water was effective in removing pyrogenetic substances.

The material prepared as described in Example 2 was subjected to a further pyrogen test by rinsing a 2 gm sample four times with 20 ml portions of pyrogen free, distilled water. After the fourth rinse, the sample was placed in 20 ml of pyrogen free, distilled water and held for 2 hours at 48° C. The sample was removed and portions of the holding solution injected into three rabbits and changes in the body temperatures noted as described above. The temperature changes were as shown in Table 3.

Table 3

| Rabbit | Temperature Change, °C. | | | | |
|---|---|---|---|---|---|
| | 1st hr. | 2nd hr. | 3rd hr. | Total Change | Max. Change |
| G | 0.0 | 0.0 | +0.3° | +0.3° | +0.3° |
| H | +0.1° | 0.0 | +0.2° | +0.3° | +0.2° |
| I | +0.2° | +0.3° | +0.3° | +0.8° | +0.3° |
| | | | Total for 3 rabbits | +1.4° | |

The test confirmed that the sample was non-pyrogenic. Although the total change in temperature of the rabbits was +1.4° C., it will be noted that the maximum temperature change for any rabbit in a one hour period was only +0.3° C.

As shown by the foregoing examples, the washing sequence involving washing with aqueous ethanol followed by washing with pyrogen free water is critical in the removal of pyrogenic substances. As specifically illustrated in Example 2, two washings with aqueous ethanol were utilized prior to the final pyrogen free water washing. The first aqueous ethanol washing may be replaced by washing with pyrogen free water and thus reduce the cost of the washing procedure. Such pyrogen free water washing, however, must be followed by a washing with aqueous ethanol prior to the final washing with pyrogen free water.

The pyrogen free corium may be converted into a fluffy mass of fibers as described in the aforementioned patent. The wet corium may be diced or chopped into small fragments or chips of one-fourth to one-half inch (6.4 to 12.7 mm) sizes in a cutting mill, such as, for example, an Urschel Mill. The chips may be slurried in aqueous ethanol (70% pyrogen free water and 30% ethanol, by weight) including the water contained in the chips. After separating the chips from excess liquid, they are slurried in ethanol to which has been added an ionizable acid, such as hydrochloric acid, in an amount sufficient to form a partial salt of collagen containing from about 50 to 90% of the theoretical stoichiometric bound acid content. Slurrying is continued for a period sufficient to form the partial salt and the reacted chips recovered. The reacted chips are subsequently slurried in ethanol and separated from the liquid in a sufficient number of cycles until the water content of the chips has been reduced to 1 to 2%. The chips are dried by oven or vacuum drying to a volatiles content of 1%. Following conditioning to a moisture content of 8 to 15%, the chips are fiberized and deaggregated to form a fluffy, fibrous mass. Prior to use, the fibrous mass is subjected to a sterilization treatment as by heating.

Although the invention has been illustrated specifically as applied to corium and the conversion of the pyrogen free corium to a fluffy fibrous product, the method is equally applicable to the treatment of other collagen containing materials such as, for example, sinews, tendons, cartilage, bones and the like and to medical products other than the fluffy fibrous product.

What is claimed is:

1. The method for producing pyrogen free collagen which comprises removing mechanically foreign substances from the surfaces of the collagen while in contact with an aqueous solution of an alkalie or alkaline earth metal hypochlorite, washing the collagen with an aqueous ethanol solution and thereafter washing the collagen with pyrogen free water.

2. The method as defined in claim 1 wherein the aqueous hypochlorite solution is an aqueous solution of sodium hypochlorite.

3. The method as defined in claim 2 wherein the aqueous solution contains from about 50 to 250 ppm of sodium hypochlorite.

4. The method as defined in claim 1 wherein the aqueous ethanol solution contains about 30 to 90% ethanol by volume and 70-10% water by volume.

5. The method as defined in claim 1 wherein the aqueous hypochlorite solution is an aqueous solution of sodium hypochlorite containing from about 50 to 250 ppm sodium hypochlorite and the aqueous ethanol solution contains about 30 to 90% ethanol by volume and 70 to 30% water by volume.

6. The method as defined in claim 1 wherein the collagen is corium.

7. The method as defined in claim 6 wherein the foreign substances are removed from the corium surfaces by brush washing the corium surfaces while in contact with an aqueous solution of sodium hypochlorite.

8. The method as defined in claim 6 wherein the corium is derived from hides washed with an aqueous solution of sodium hypochlorite containing from 50 to 250 ppm sodium hypochlorite and the flesh and graid sides of the hide are removed to recover the corium.

9. The method as defined in claim 8 wherein foreign substances are removed from the corium surfaces by brush washing the surfaces while in contact with an aqueous solution containing from about 50 to 100 ppm sodium hypochlorite and the aqueous ethanol solution contains about 70% ethanol by volume and 30% water by volume, the solutions having a temperature not exceeding about 40° C.

10. The method as defined in claim 9 wherein the temperature of the solutions is between the freezing point and 25° C.

11. As an article of manufacture, pyrogen free collagen prepared by the method as defined in claim 1.

12. An article of manufacture as defined in claim 11 wherein the collagen is corium.

* * * * *